(12) United States Patent
Berreklouw

(10) Patent No.: US 7,172,605 B2
(45) Date of Patent: Feb. 6, 2007

(54) APPLICATOR FOR A PROSTHESIS ASSEMBLY COMPRISING SUCH AN APPLICATOR AND FIXTURE SYSTEM FOR LOADING SUCH AN APPLICATOR

(76) Inventor: Eric Berreklouw, Ardennenlaan 13, NL-5691 JN Son (NL)

( * ) Notice: Subject to any disclaimer, the term of this patent is extended or adjusted under 35 U.S.C. 154(b) by 585 days.

(21) Appl. No.: 10/480,452

(22) PCT Filed: Jun. 14, 2002

(86) PCT No.: PCT/NL02/00395

§ 371 (c)(1),
(2), (4) Date: Dec. 12, 2003

(87) PCT Pub. No.: WO03/003926

PCT Pub. Date: Jan. 16, 2003

(65) Prior Publication Data

US 2004/0199176 A1    Oct. 7, 2004

(30) Foreign Application Priority Data

Jun. 15, 2001   (NL) .................................... 1018302

(51) Int. Cl.
*A61B 17/00* (2006.01)
(52) U.S. Cl. ...................... 606/142; 606/108
(58) Field of Classification Search ............... 606/108, 606/142, 191, 198, 200; 623/1.11, 1.12
See application file for complete search history.

(56) References Cited

U.S. PATENT DOCUMENTS 5,026,377 A    6/1991   Burton et al.
6,152,937 A   11/2000   Peterson et al.
6,241,655 B1   6/2001   Riess

FOREIGN PATENT DOCUMENTS

| WO | WO 99/38454 | 8/1999 |
| WO | WO 00/24339 | 5/2000 |
| WO | WO 00/44311 | 8/2000 |

*Primary Examiner*—Anhtuan T. Nguyen
*Assistant Examiner*—Marlee C. Foster
(74) *Attorney, Agent, or Firm*—Buchanan Ingersoll & Rooney, PC

(57) ABSTRACT

The present invention relates to an applicator for a prosthesis of the type having a tubular element and distal and proximal flange fingers which are arranged distributed around the periphery of the tubular element and can be brought into a straightened position under spring tension for fitting the prosthesis. The applicator comprises a carrier tube with, at the distal end thereof, a supporting ring that fits in the tubular element; a movable release rod that is housed in the carrier tube and has a distal release ring at the distal end. The distal release ring is provided with an undercut that opens in the proximal direction, extends around the periphery and has an internal peripheral surface facing inwards. This internal peripheral surface lies within or on the outer contour of the external peripheral surface of the supporting ring. The invention furthermore relates to an assembly of such an applicator with a tubular element clamped thereon as well as to a fixture system for fitting the tubular element on the applicator.

17 Claims, 4 Drawing Sheets

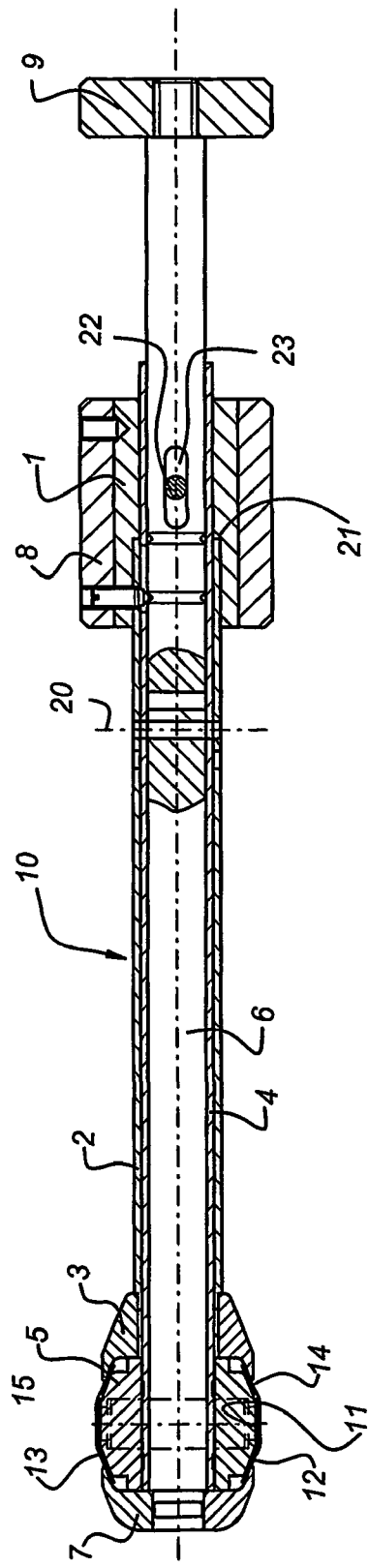
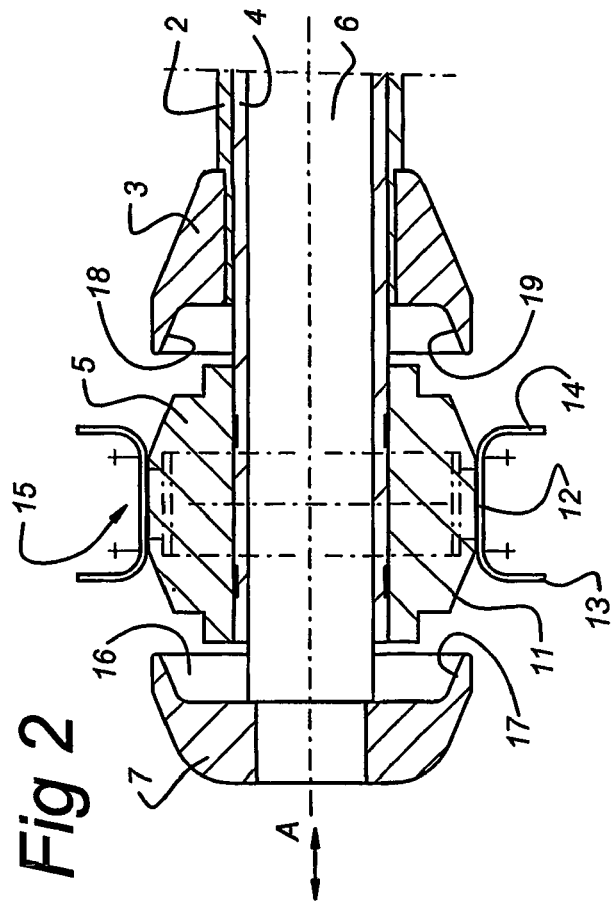
Fig 1
Fig 2

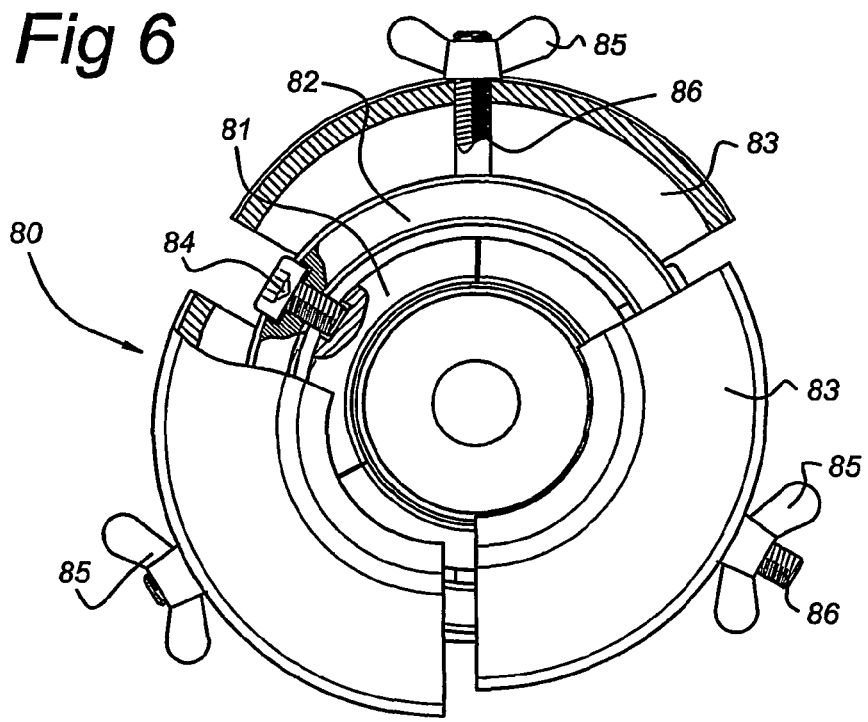
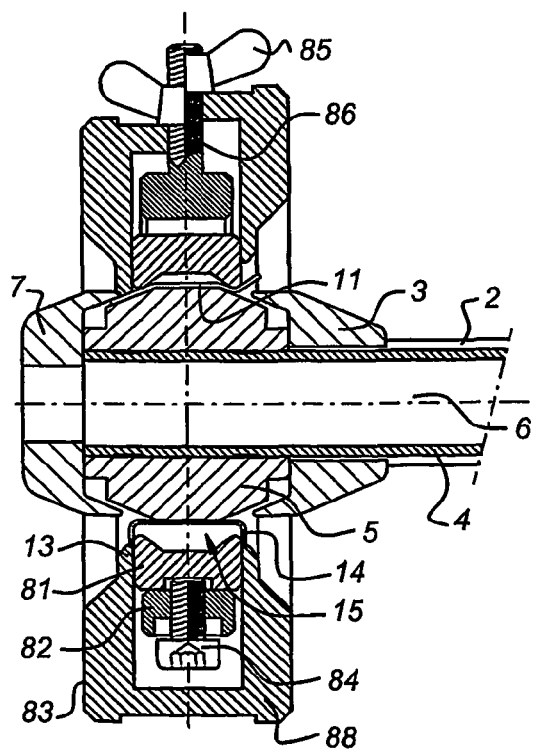
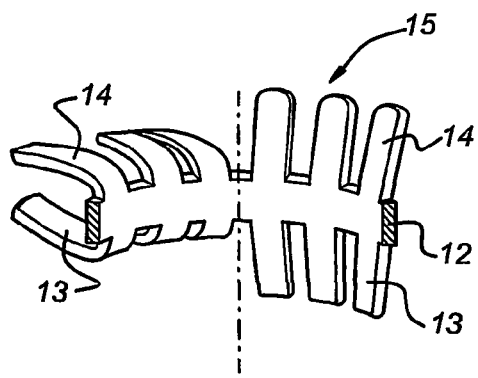

APPLICATOR FOR A PROSTHESIS ASSEMBLY COMPRISING SUCH AN APPLICATOR AND FIXTURE SYSTEM FOR LOADING SUCH AN APPLICATOR

This application is a National Stage of PCT/NL02/00395, which claims priority to The Netherlands Patent Publication No. 1018302, filed on Jun. 15, 2001, the contents of which are herein incorporated in their entirety.

The present invention relates to an applicator for a prosthesis. According to the invention this prosthesis is of the type having a tubular element provided with distal and proximal flange fingers arranged distributed around the periphery of the tubular element, at least the distal flange fingers, preferably the distal and proximal flange fingers, of which can be or have been reversibly bet, against a resilient force, from a position projecting outwards with respect to the tubular element into a straightened position in which the projection of the respective flange fingers on a radial transverse plane of the tubular element is essentially on or within the periphery of the tubular element. Tubular elements of this type are disclosed in WO 00/24339 and WO 00/44311, both in the name of the same Applicant as the present application. As far as the prostheses are concerned, these two WO applications are therefore also incorporated in the present application by reference. WO 00/24339 relates in particular to vascular prostheses and specifically in particular to coupling means for joining blood vessels and/or vascular prostheses or other types of tubular canals in the human or animal body to one another. WO 00/44311 has our main sections having as their subject prostheses for which the applicator according to the present invention can be used. The first and second sections in WO 00/44311 relate in particular to valve prostheses for heart valves or at least fixings for heart valve prostheses, the third section relates to vascular connections and the fourth section to both valve and vascular connections. What is concerned with all these prostheses is, in particular, that there is a tubular element with so-called bottom and top flange fingers. In the present application these bottom and top flange fingers are designated as, respectively, distal and proximal flange fingers. Here the terms "distal" and "proximal" relate in particular to the applicator, which, as will also be seen, has an elongated projection section, the free end of which is designated the distal end and, correspondingly, the opposing direction is designated proximal. The essential feature of the distal flange fingers of the tubular element is that for positioning in a passage—which impedes the passage of flange fingers pointing radially outwards—these arms can be brought into and held in the straightened position in order to be able to spring back again under resilient force from said straightened position into a position pointing radially outwards. Within the scope of the present invention the prostheses can be either prostheses made of nitinol materials or similar memory materials which can be bent from a first position into a second position and can be frozen in said second position in order then to be able to spring back into the first position after a specific temperature has been exceeded or also more conventional flange fingers which can be bent into the straightened position against resilient force, which flange fingers are then held in said straightened position by a mechanical, physical restraint in order to be able simply to bend back into their initial position under the influence of the resilient force after said restraint is removed. As is indicated in the Applicant's cited WO applications, such flange fingers can, for example, be held straight by a small pipe that is located around the outside and is retracted, by a cord around the flange fingers or in some other way.

The aim of the present invention is to provide an applicator for, in particular, fitting prostheses of the type mentioned in the preamble, very particularly valve prostheses for heart valves, which applicator enables highly accurate and reliable positioning of the prosthesis and also ensures reliable release of the prosthesis such that following release—that is to say allowing the flange fingers to spring back into a position pointing outwards—the prosthesis is firmly and correctly anchored in the sounding tissue.

The abovementioned aim is achieved according to the invention in that the applicator comprises:

a carrier tube having, at the distal end thereof, a supporting ring that fits inside the tubular element and has an external peripheral surface suitable for supporting said tubular element;

a release rod that is housed in the carrier tube, can be moved with respect thereto and has, at the distal end, a distal release ring;

wherein the distal release ring has an undercut that opens in the proximal direction, extends around the periphery and has a fist internal peripheral surface facing inwards, and wherein said first internal peripheral surface is located inside or on the outermost contour of the external peripheral surface of the supporting ring.

The carrier tube is provided at its free end, the distal and, with a supporting ring that fits in the prosthesis to be fitted for supporting the prosthesis to be fitted. By means of the carrier tube the prosthesis can then be positioned in the correct position from some distance away. During first positioning the distal—related to the orientation of the carrier tube-flange fingers are in the straightened position and at least the ends thereof are located in the undercut in the distal release ring in order to ensure that they are unable to move from said straightened position. With this arrangement the distal release ring will then primarily act as a mechanical, physical restraint for the straightened distal flange fingers. In the case of the use of nitinol, however, it is also very readily conceivable that these distal flange fingers have already straightened out themselves and require no physical restraint for holding in said straightened position. In such a case the release ring will then primarily act during positioning as a safety device should the straightened, frozen position be lost prematurely. With this arrangement the distal release ring can then optionally be retracted after the correct position has been reached, after which the frozen state can be terminated. However, it is also conceivable first to terminate the frozen state, so that from that point in time the release ring will act as a physical, mechanical restraint. When the release act as a physical, mechanical restraint and is then retracted in order to release the distal flange fingers, these distal flange fingers will then as it were be discharged under the influence of their resilient force in order to spring back from the straightened position into the position pointing outwards. As far as the retraction or at least moving of the distal release ring with respect to the carrier tube is concerned, it is pointed out that this could be achieved by turning the distal release ring with respect to the carrier tube. In such a case the distal release ring will have proximally oriented pin-like elements which on an underside define the first internal peripheral surface facing inwards and have gaps between them of a width at least equal to that of the distal flange fingers, such that said distal flange fingers are able to pass through them.

In order to facilitate the introduction of the applicator with prosthesis into a blood vessel or other type of body canal and then to move the applicator with prosthesis through said blood vessel or body canal, it is preferable according to the invention to construct the external distal surface of the distal release ring such that it tapers, for example conically, in the distal direction. This makes it possible to dilate the surrounding tissue.

However, according to the invention it is preferable if the release rod with the distal release ring can be moved from a proximal position holding the distal flange fingers straight to a distal position relying the distal flange fingers. Such a movement in the longitudinal direction of the carrier tube is always easier to achieve in a reliable manner than is tuning with respect to the carrier tube.

According to a further preferred embodiment, it is advantageous if, when the distal release ring is in the proximal position, the first internal peripheral surface of the distal release partially overlaps the external peripheral surface of the supporting ring. In this way the tubular element can be reliably held fixed on the supporting ring while the prosthesis is brought into its intended position.

In order to prevent damage to the distal flange fingers when the tubular element is held on the applicator, it is preferable according to the invention if the first internal peripheral surface of the distal release ring and the external peripheral surface of the supporting ring run parallel to one another in the overlap region. In this way a gap of constant width can be created between the two peripheral surfaces, within which gap the distal flange fingers can then be accommodated without any local pinching forces.

In order to be able to keep the external dimensions of the applicator as a whole as small as possible, it is preferable according to the invention if the first internal peripheral surface of the distal release ring tapers preferably conically, in the distal direction. The distal flange fingers are then able, as it were, to be brought into a straightened position in which they come to lie completely within the outer contour of the tubular element. The release ring that still has to engage around the distal flange fingers can then be given external dimensions of the same order of magnitude as, or possibly somewhat smaller than, those of the tubular element. This is advantageous when bringing the prosthesis into its intended position. Correspondingly, according to the invention it is furthermore advantageous if the external peripheral surface of the supporting ring has a distal zone that tapers, preferably conically, in the distal direction.

If the proximal flange fingers of the prosthesis can also be brought into a straightened position for guiding said prosthesis into the intended position, it is preferable according to the invention if the applicator fiber comprises a release tube that is fitted on the carrier tube and can be moved with respect thereto and has a proximal release ring at the distal end, wherein the proximal release ring has an undercut that opens in the distal direction extends around the periphery and has a second internal peripheral surface facing inwards, and wherein said second internal peripheral surface is located inside or on said outermost contour of the external peripheral surface of the supporting ring. As far as the mode of action and the manner of release by means of this proximal release ring are concerned, it will be clear to all that everything that has been explained with regard to the distal release ring also applies for this, with the proviso that in the case of moving along the carrier tube for the purposes of release the proximal release ring will move in a direction opposed to that of the distal release ring. The same essentially also applies for everything that has been explained with regard to the shape of the distal release ring, independently or in relation to the shape of the external peripheral surface of he supporting ring. This also is, as it were mirrored, also applicable to the proximal release ring. Thus, the proximal release ring can also be constructed such that it can be teed with respect to the carrier tube, in which case this proximal release ring will then comprise distally oriented pin-like elements that, on the underside, define the second internal peripheral surface facing inwards and have, gaps between them of a width at least equal to that of the proximal flange fingers, such that the latter are able to pass through these gaps.

In order to be able to preclude premature release of the distal or proximal flange fingers of the prosthesis, it is preferable according to the invention if the applicator has locking means for locking the distal release ring in the proximal position with respect to the carrier tube, as well as, preferably, also locking the proximal release ring in the distal position with respect to the carrier tube. It will be clear to those skilled in the art that such locking means can be implemented in a wide variety of ways. In a simple and advantageous embodiment provision is made that the locking means comprise a pin that can be inserted through passages that are aligned in the proximal and the distal position, respectively, in the carrier tube, the release rod and, respectively, the release tube. In this way a single locking pin is used. It is, of course, also conceivable to use two locking pins by means of which the release rod and the release tube can each individually be locked with respect to the carrier tube.

The present invention furthermore also relates to an applicator according to the invention which is provided with a prosthesis, of the type as described in the first paragraph of this application, fitted thereon, wherein the distal flange fingers and preferably also the proximal flange fingers are in the straightened position. In order to restrict to a minimum the actions carried out by the specialist or surgeon and at the same time also to be able to preclude errors or deficiencies in such actions, it is advantageous to market the applicator with the prosthesis to be fitted already clamped thereon in advance in the factory.

The present invention also relates to an assembly of an applicator according to the invention and a stand to which the applicator is fixed or can be fixed, wherein the stand is fixed or at least can be fixed to a sternum spreader, an operating table or a fixed reference point in an operating theatre, wherein the stand comprises a lockable arm and joint system with preferably three orthogonal degrees of translational freedom and/or three orthogonal degrees of rotational freedom. Included in this is also understood to be a stand that is fixed, for example, to the ceiling of an operating theatre and optionally can be moved in the same way as a crab or in scene other way completely freely over the ceiling. The fixed reference point will then be the fixed reference point with respect to which the crab operates. This fixed reference point can then be, for example, the floor, the ceiling, a wall or a corner of the operating theatre.

In addition, the present invention also relates to a fixture system for cramps a prosthesis, of the type as described in the first paragraph of this application, on an applicator according to the invention, wherein said fixture system according to the invention comprises:

an inner ring subdivided into three or more segments;

a one-piece central ring; and an outer ring subdivided into three or more segments;

wherein the central ring has, per inner ring segment, a radial threaded bore with inner tightening screw the radial inside end of which engages on the respective inner ring segment, wherein the central ring has, per outer ring segment, an outer tightening screw, which outer tightening screw protrudes through a radial bore in the respective outer ring segment so that the head of the outer tightening screw or a nut element engages from the outside on said outer ring segment, the outer ring segments having an L-shape or U-shape viewed in the axial cross-sectional plane and wherein the radial arms of said L-shape or U-shape run radially over the central ring and inner ring in at least that portion of he outer ring segments in which the latter are tightened radially inwards.

The present invention will be explained in more detail below with reference to illustrative embodiments shown in the drawing.

In the drawing:

FIG. 1 shows a diagrammatic longitudinal sectional view of an applicator according to the invention with a prosthesis clamped thereon, in a position suitable for fitting;

FIG. 2 shows, as a detail, the distal end of FIG. 1, but with the applicator and prosthesis now in the completely released position;

FIG. 6 shows a diagrammatic perspective view of a fixture system according to the invention;

FIG. 7 shows a diagrammatic longitudinal sectional view of the distal end of the applicator according to the invention in conjunction with a fixture system according to the invention; and FIG. 8, shows, for illustration, an example of a prosthesis that can be fitted using the applicator according to the invention.

Figure 3:
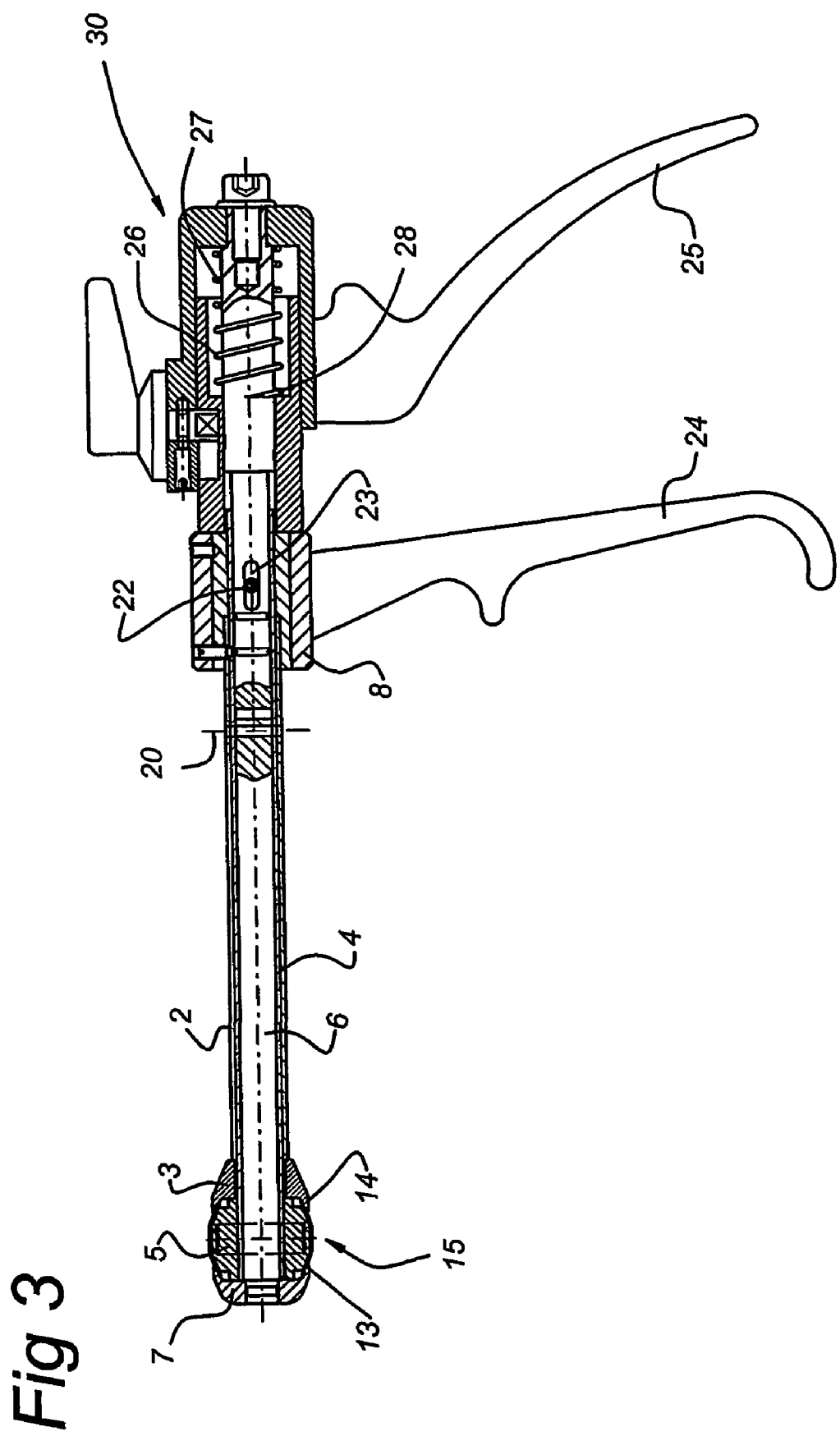
FIG. 3 shows, in longitudinal section, an example of a further applicator according to the invention.

FIG. 1 shows an applicator 10 according to the invention The applicator comprises a carrier tube 4 with a supporting ring 5 at the distal end thereof. This supporting ring 5 has an external plane 11 that is shaped such that it fits precisely inside the tubular element 12.

With reference to FIG. 8, in which an example of a prosthesis 15 of the type according to the invention—but which prosthesis can also be open—is shown for the purposes of illustration only, the prosthesis 15 is made up of a tubular element 12, that usually is in the form of a closed ring with lower flange fingers 13 and upper flange fingers 14, which in the present application are referred to as, respectively, distal flange fingers 13 and proximal flange fingers 14. In the right-hand half of FIG. 8 the flange fingers 13, 14 are shown in the straightened position (see the view of the prosthesis 15 in FIG. 1) and in the left-hand half of FIG. 8 they are shown in a position pointing radially outs (see the view of the prosthesis 15 in FIG. 2).

Returning to FIG. 1, a release rod 6 is housed in the carrier tube 4, which release rod 6 can be solid; as shown, but equally well can also be of hollow construction. A hollow construction has the advantage that this makes it possible to fit the applicator on a guide wire, along which the applicator can be guided to its intended position in the body. The distal and proximal ends of the applicator will then be open in order to feed the guide wire through the hollow release rod. A distal release ring 7 is provided at the distal end of the release rod 6. The distal release ring 7 is—see in particular FIG. 2—provided with an undercut 16 that opens in the proximal direction and has a first internal peripheral surface 17 facing inwards. The release rod 6 can be moved, together with the distal release ring 7, back and forth with respect to the carrier tube 4, in the direction of double-headed arrow A, between a proximal position shown in FIG. 1 and a distal position shown in FIG. 2.

A release tube 2 that carries a proximal release ring 3 at is distal end is provided around the carrier tube 4. The proximal release ring 3 is—see in particular FIG. 2—provided with an undercut 18 that opens in the distal direction and has a second internal peripheral surface 19. The release tube 2, together with the proximal release ring 3, can be moved back and forth with respect to the carrier tube 4, in the direction of double-headed arrow A, between a distal position shown in FIG. 1 and a proximal position shown in FIG. 2.

The external peripheral surface 11 of the supporting ring 5 is provided on its distal side with a plane tapering in the distal direction and on its proximal side with a plane section tapering in the proximal direction. In this way it is possible to fix the distal flange fingers 13 and, respectively, proximal flange fingers 14 on the supporting ring 5 in a straightened position taper inwards. In this position the distal flange fingers 13 are held in the straightened position taping inwards because the first internal peripheral surface 17 of the undercut 16 in the distal release ring 7 engages from the outside on said distal flange fingers 13 in order to prevent them from springing back outwards. In a corresponding manner the proximal release ring 3 holds the proximal flange fingers 14 in their straightened position taps inwards because the internal peripheral surface 19 of the proximal release ring 3 engages from the outside on the ends of the proximal flange fingers 14. In this clamped position, ready for fitting—as is shown in FIG. 1—the release tube 2 with proximal release ring 3, the release rod with distal release ring 7 and the carrier tube 4 can be fixed with respect to one another by means of a pin 20 that extends through passages that are aligned in this position in, successively, the release tube 2, the carrier tube 4 and the release rod 6. As can be seen in FIG. 1, the external diameter of the applicator with a prosthesis 15 clamped thereon is determined, at least at the distal end of the applicator, by the external peripheral dimensions of the tubular element 12 of the prosthesis 15.

When the distal end of the applicator 10—the left-hand section in FIG. 1—with the prostheses 15 clamped thereon has been positioned in its intended position—the release rings 3 and 7 of the supporting ring 5 can be reacted in order to release the flange fingers 13 and 14 so that they are able to spring back into the outward-pointing position as, for example, is shown in FIG. 2. To this end the following procedure can be used with the applicator 10 from FIG. 1: the locking pin 20 is removed, the block 8 is pulled in the proximal direction towards button 9 in order in this way to slide the release tube 2 with proximal release ring 3 in the proximal direction until the proximal flange fingers 14 have been released and the release tube 2 comes into contact with the stop plane 21. The button 9 can then be pressed in in the distal direction so that the distal release ring 7 moves in the distal direction and releases the distal flange fingers 13. The movement of the button 9 and release rod 6 is limited by the stop pin 22 which is supported in a bearing in the carrier tube 4. If it protrudes from the carrier tube 4, this pin 22 can also be used as limiting stop for the release tube 2, in which case this release tube 2 will then also have been provided with a slot corresponding to the slot 23 in release rod 6. As will be clear, it is also possible to adopt the reverse procedure in the sense that the button 9 is first pressed in the distal direction and the block 8 is then pulled in the proximal direction. It is also pointed out that block 8 and button 9 can also move towards one another at the same time, which will work particularly well when the carrier tube 4 is, as will be discussed in more detail below, fixed with respect to the surrounding to, for example, a sternum spreader, the operating table or is otherwise fixed with respect to, for example, the operating theatre.

FIG. 3 shows a variant of an applicator according to the invention, which applicator is indicated in its entirety by 30. The applicator 30 differs from the applicator 10 essentially in respect of the operating mechanism. The distal end of the applicator 30 is constructed correspondingly to the distal end of the applicator 10 in FIG. 1. Accordingly, the same reference numerals have been used for corresponding components and a number of reference numerals, in particular the reference numerals from FIG. 2, have not been included in FIG. 3. The difference in operating mechanism is essentially that a sort of pistol grip is provided. This pistol grip consists of a handle 24 that is fixed to block 8 as well as a handle 25 that takes the place of button 9 in FIG. 1. By now, after releasing the lock by turning knob 26 and/or removing the locking pin 20, which may be present, squeezing the handles 24 and 25 towards one another the proximal release ring 3 and distal release ring 7 can be moved away from the supporting ring 5 in such a way that the distal and proximal flange fingers 13 and 14, respectively, of the prosthesis 15 are released. The operating mechanism also comprises a spring 26 which on one side, at 27, engages on the release rod 6 and on the other side, at 28, engages on the release tube 2. This spring 26 can operate in two ways. On the one hand, it is conceivable that a spring tension is built up in the spring on squeezing the handles 24 and 25 towards one another, such that the handles 24 and 25 are moved apart again after they are released. On the other hand, it is also very readily conceivable to place the spring 26 under pretension in advance and to use this pretension of the spring 26 to move the release ring 3 and release ring 7 away from the supporting ring 5. In other words, the pretension in the spring 26 is then used to release the distal and proximal flange fingers 13, 14. Very rapid release of said flange fingers can be achieved in this way. This release is then prevented by holding the handles 24 and 25 together with the hand. Especially in this case the locking pin 20 will be able to offer supplementary help since this pin can then hold the release rod 6, the carrier tube 4 and the release tube fixed with respect to one another so that the strain on the hand holding the handles 24 and 25 is zero until the locking pin 20 has been removed. This will therefore be able appreciably to increase the ease of use of the applicator 30.

Figure 4:
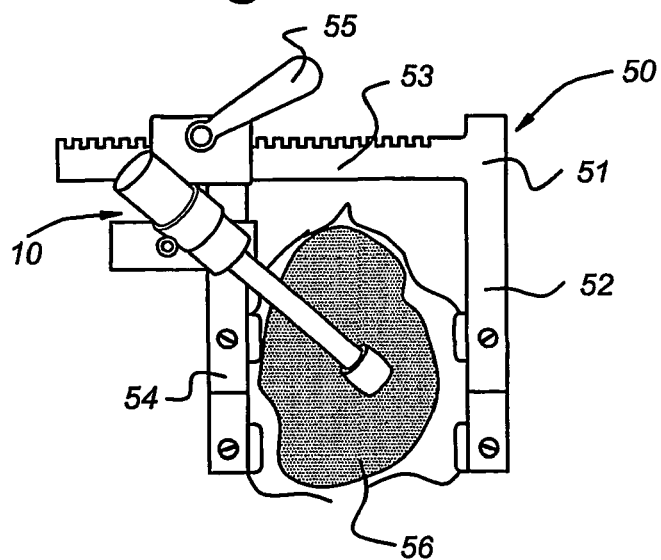
FIG. 4 shows, diagrammatically, a first assembly according to the invention.

FIG. 4 shows, highly diagrammatically, by way of example an applicator 10 according to the invention, that is not shown in more detail, fixed on a sternum spreader 50 known per se. The sternum spreader 50 shown as an example consists of an L-shaped part 51 with a first spreader arm 52 and guide arm 53, on which a second spreader arm 54 is mounted such that it can be moved by means of an adjusting lever 55. With this arrangement the spreader arms 52 and 54 serve for pushing apart the sternum, which has first been split for this purpose, in order to make the heart 56 accessible for an operation. By fixing the applicator 10 to the sternum spreader, directly or with a stand with lockable arms and/or joints placed between than, the applicator is able to be stabilized and held still with respect to the location where the prosthesis has to be positioned.

Figure 5:
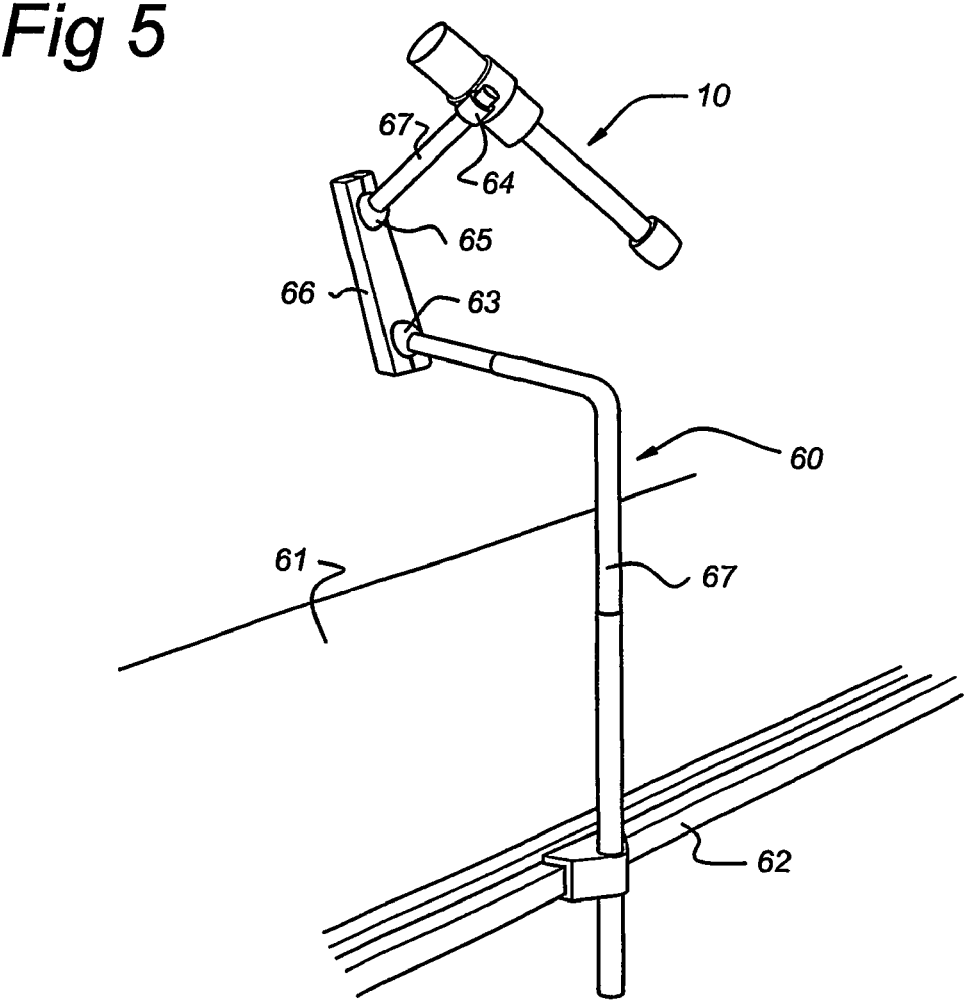
FIG. 5 shows, diagrammatically, a second assembly according to the invention.

FIG. 5 shows, highly diagrammatically, by way of example an applicator 10 which has been fixed to an operating table 61 by means of a stand 60. The stand 60 can be moved along a guide rod 62 in the longitudinal direction of the operating table 61 and is also provided with a ball joint 63, a ball join 65 and a linear joint 64 with the necessary arms 66 and 67 between them, which arms can optionally also be adjustable in the longitudinal direction. The main supporting arm of the stand consists of an L-shaped bar 67, the two arms of which are preferably telescopic, as is indicated diagrammatically.

When a stand is used, stand and applicator can form an integral whole or can be coupled to one another, and preferably also uncoupled from one another, by means of a coupling, such as a snap-fit connection.

FIGS. 6 and 7 show a fixture system for mounting a prosthesis 15 on the distal end of an applicator 10, 30. This fixture system 80 consists of an inner ring made up of three segments 81, a one-piece middle ring 82 and an outer ring made up of three segments 83. The segments 81 and 83 extend over arcs of approximately 120°. As can be seen in FIG. 7, in particular at the bottom, the outer ring segments 83 are U-shaped in axial longitudinal section in order completely to engage around the middle ring 82 and inner ring segments 81 on either side. The inner ring segments 81 can be manipulated with respect to the middle ring 82 by means of set screws 84. The set screws 84 interact by means of screw thread with the middle ring 82 in order for their radial inner ends to be able to push the inner ring segments 81 inwards. The inner ring segments 81 thus serve to fix the prosthesis 15 with respect to the supporting ring 5 and in particular to press the prosthesis firmly down onto this ring; see top of FIG. 7. As can be seen at the bottom of FIG. 7, the width of the inner ring segments 81 viewed in the axial direction is such that this fits between the outward-pointing flange fingers 13 and 14, in particular here fits between these arms just with some play or just without play. By exerting pressure on the inner ring segments 81, as can be seen at the top of FIG. 7, the flange fingers 13 and 14 am indeed somewhat forced in the direction of a straightened position—see the right-hand side at the top of FIG. 7—but these arms are not completely straightened as is needed in order to be able to be accommodated in the undercuts in the release rings 3 and 7. The outer ring segments 83 are then pressed radially inwards by means of wing nuts 85 and bolt pins 86 rigidly fixed to the middle ring in order to press the flange fingers flat against the tapering distal and, respectively, proximal edge zone of the outer peripheral surface 11 of the supporting ring 5, as is shown top left in FIG. 7. As soon as this has taken place, the release rings 3 and 7 will be moved towards the supporting ring 5 in order to accommodate the flange fingers 13 and 14 in the undercuts thereof, in order to prevent them from springing back.

In order to save work for the surgeon and to be able to guarantee faultless clamping of prostheses, it is preferable that clamping of the prosthesis 15 on the applicator is already carried out in the factory. However, it is also conceivable that the surgeon or other technical staff clamps a prosthesis 15 on the applicator according to the invention during the operation or very shortly before the operation.

Although this may possibly not be readily suspected from the above description of the figures, it must be pointed out that for the prosthesis 15 use can be made of elements produced from nitinol which can be frozen in the position shown in FIG. 1. In this case the release rings 3 and 7 will in the first instance provide an additional safety feature against the flange fingers 13 and 14 intentionally popping outwards. With such an application it is conceivable to move the release rings 3 and 7 away from the supporting ring 5 and only then to terminate the so-called frozen state so that the flange fingers 13 and 14 pop back outwards. However, it is also conceivable first to terminate the frozen state and only then to retract the release rings 3 and 7 from the supporting ring 5 so that the flange fingers 13 and 14 pop outwards immediately. In this context it is pointed out for the sake of completeness that in the case of the embodiment shown in FIGS. 1 and 2 and 3 the intention is primarily that the flange fingers 13 and 14 will be permanently in contact, under spring tension, with the internal peripheral surfaces 17 and 19 of the undercuts 16 and 18 of the distal and, respectively, proximal release ring 7, 3.

In order to facilitate movement of the applicator through curved canals, it can be highly advantageous according to the invention to make the applicator, in particular carrier tube, the release rod and release tube, curved or deformable.

The invention claimed is:

1. Applicator for a prosthesis having a tubular element provided with distal and proximal flange fingers arranged distributed around the periphery of the tubular element, at least one of the distal flange fingers and the proximal flange fingers, adapted to be reversibly bent, against a resilient force, from a position projecting outwards with respect to the tubular element into a straightened position in which the projection of the respective flange fingers on a radial transverse plane of the tubular element is substantially on or within the periphery of the tubular element, wherein the applicator comprises:

a carrier tube having, at the distal end thereof, a supporting ring that fits inside the tubular element and has an external peripheral surface suitable for supporting said tubular element;

a release rod that is housed in the carrier tube, can be moved with respect thereto and has, at the distal end, a distal release ring;

wherein the distal release ring has an undercut that opens in the proximal direction, extends around the periphery and has a first internal peripheral surface facing inwards, and wherein said first internal peripheral surface is located inside or on the outermost contour of the external peripheral surface of the supporting ring.

2. Applicator according to claim 1, wherein the release rod with the distal release ring can be moved from a proximal position holding the distal flange fingers straight to a distal position releasing the distal flange fingers.

3. Applicator according to claim 1, wherein when the distal release ring is in the proximal position, the first internal peripheral surface of the distal release ring partially overlaps the external peripheral surface of the supporting ring.

4. Applicator according to claim 3, wherein the first internal peripheral surface of the distal release ring and the external peripheral surface of the supporting ring run parallel to one another in the overlap region.

5. Applicator according to claim 1, wherein the first internal peripheral surface of the distal release ring tapers, preferably conically, in the distal direction.

6. Applicator according to claim 1, wherein the external peripheral surface of the supporting ring has a distal zone that tapers, preferably conically, in the distal direction.

7. Applicator according to claim 1, wherein the external distal plane of the distal release ring tapers, such as conically, in the distal direction.

8. Applicator according to claim 1, wherein the applicator further comprises a release tube that is fitted on the carrier tube and can be moved with respect thereto and has a proximal release ring at the distal end, wherein the proximal release ring has an undercut that opens in the distal direction, extends around the periphery and has a second internal peripheral surface facing inwards, and wherein said second internal peripheral surface is located inside or on the outer contour of the external peripheral surface of the supporting ring.

9. Applicator according to claim 8, wherein the release tube with the proximal release ring can be moved from a distal position holding the proximal flange fingers straight to a proximal position releasing the proximal flange fingers.

10. Applicator according to claim 8, wherein when the proximal release ring is in the distal position, the second internal peripheral surface of the proximal release ring partially overlaps the external peripheral surface of the supporting ring.

11. Applicator according to claim 10, wherein the second internal peripheral surface of the proximal release ring and the external peripheral surface of the supporting ring run parallel to one another in the overlap region.

12. Applicator according to claim 8, wherein the second internal peripheral surface of the proximal release ring tapers, preferably conically, in the proximal direction.

13. Applicator according to claim 8, wherein the external peripheral surface of the supporting ring has a proximal zone that tapers, preferably conically, in the proximal direction.

14. Applicator according to claim 1, wherein the applicator has locking means for locking the distal release ring in the proximal position with respect to the carrier tube, as well as, preferably, also locking the proximal release ring in the distal position with respect to the carrier tube.

15. Applicator according to claim 14, wherein the locking means comprise a pin that can be inserted through passages that are aligned in the proximal and the distal position, respectively, in the carrier tube, the release rod and, respectively, the release tube.

16. Applicator according to claim 1, provided with a prosthesis fitted thereon, wherein the distal flange fingers and preferably also the proximal flange fingers are in the straightened position.

17. Assembly of an applicator according to claim 1 and a stand to which the applicator is fixed or can be fixed, wherein the stand is fixed or at least can be fixed to a sternum spreader, to an operating table or with respect to a fixed reference point in an operating theatre, and wherein the stand comprises a lockable arm and joint system that, preferably, has three orthogonal degrees of translational freedom and/or three orthogonal degrees of rotational freedom.

* * * * *